(12) United States Patent
Wen et al.

(10) Patent No.: US 12,036,251 B2
(45) Date of Patent: Jul. 16, 2024

(54) STRAIN FOR PREVENTING AND TREATING METABOLIC DISEASES AND USE THEREOF

(71) Applicants: SPH SINE PHARMACEUTICAL LABORATORIES CO., LTD, Shanghai (CN); SHANGHAI INSTITUTE OF ENDOCRINE AND METABOLIC DISEASES, Shanghai (CN)

(72) Inventors: Bin Wen, Shanghai (CN); Guang Ning, Shanghai (CN); Xin Ma, Shanghai (CN); Weiqing Wang, Shanghai (CN); Hongjing Yu, Shanghai (CN); Jie Hong, Shanghai (CN); Ningyun Sun, Shanghai (CN); Jiqiu Wang, Shanghai (CN); Peijun Yin, Shanghai (CN); Ruixin Liu, Shanghai (CN); Yuan Gao, Shanghai (CN); Shasha Wang, Shanghai (CN)

(73) Assignees: SPH SINE PHARMACEUTICAL LABORATORIES CO., LTD, Shanghai (CN); SHANGHAI INSTITUTE OF ENDOCRINE AND METABOLIC DISEASES, Shanghai (CN)

( * ) Notice: Subject to any disclaimer, the term of this patent is extended or adjusted under 35 U.S.C. 154(b) by 539 days.

(21) Appl. No.: 17/278,662

(22) PCT Filed: Sep. 25, 2019

(86) PCT No.: PCT/CN2019/107757
§ 371 (c)(1),
(2) Date: Mar. 23, 2021

(87) PCT Pub. No.: WO2020/063646
PCT Pub. Date: Apr. 2, 2020

(65) Prior Publication Data
US 2022/0031769 A1 Feb. 3, 2022

(30) Foreign Application Priority Data

Sep. 27, 2018 (CN) .......................... 201811132882.1

(51) Int. Cl.
*A61K 35/741* (2015.01)
*A61P 3/04* (2006.01)
*C12N 1/20* (2006.01)
*A61K 35/00* (2006.01)
*C12R 1/01* (2006.01)

(52) U.S. Cl.
CPC .............. *A61K 35/741* (2013.01); *A61P 3/04* (2018.01); *C12N 1/205* (2021.05); *A61K 2035/115* (2013.01); *C12R 2001/01* (2021.05)

(58) Field of Classification Search
CPC ........................ A61K 35/741; A61K 2035/115; A61K 35/74; A61K 2035/11; A61P 3/04; A61P 3/00; A61P 3/06; A61P 3/10; C12N 1/205; C12R 2001/01
See application file for complete search history.

(56) References Cited

U.S. PATENT DOCUMENTS

| 10,149,870 | B2 * | 12/2018 | Kaplan | .................. A61K 35/74 |
| 10,729,732 | B2 * | 8/2020 | Kaplan | .................. A61K 35/74 |
| 10,960,032 | B2 * | 3/2021 | O'Mahony | .............. A61K 9/00 |
| 11,338,000 | B2 * | 5/2022 | Zou | ........................ A61K 35/745 |
| 11,767,503 | B2 * | 9/2023 | Ze | ................. C12N 1/20 |
| 2015/0306152 | A1 * | 10/2015 | Cani et al. | ............. A61K 35/74 |
| 2015/0306152 | A1 | 10/2015 | Louvain | |

FOREIGN PATENT DOCUMENTS

| CN | 104918626 A | 9/2015 | |
| CN | 105106245 A | 12/2015 | |
| WO | 2014076246 A1 | 5/2014 | |
| WO | 2018/106844 A1 * | 6/2018 | ........... A61K 35/741 |

OTHER PUBLICATIONS

Marden, J., & Schilder, R. (Nov. 20, 2006). Dragonfly's metabolic disease provides clues about human obesity. EurekAlert! https://www.eurekalert.org/news-releases/764384 (Year: 2006).*
Jian, H., Liu, Y., Wang, X., Dong, X., & Zou, X. (2023). Akkermansia muciniphila as a next-generation probiotic in modulating human metabolic homeostasis and disease progression: a role mediated by gut-liver-brain axes ?. International Journal of Molecular Sciences, 24(4), 3900. (Year: 2023).*
Plovier, H., Everard, A., Druart, C., Depommier, C., Van Hul, M., Geurts, L., . . . & Cani, P. D. (2017). A purified membrane protein from Akkermansia muciniphila or the pasteurized bacterium improves metabolism in obese and diabetic mice. Nature medicine, 23(1), 107-113. (Year: 2017).*
Xu, Y., Wang, N., Tan, H. Y., Li, S., Zhang, C., & Feng, Y. (2020). Function of Akkermansia muciniphila in obesity: interactions with lipid metabolism, immune response and gut systems. Frontiers in microbiology, 11, 219. (Year: 2020).*
Dao, M. C., Everard, A., Aron-Wisnewsky, J., Sokolovska, N., Prifti, E., Verger, E. O., . . . & Micro—Obes Consortium. (2016). Akkermansia muciniphila and improved metabolic health during a dietary intervention in obesity: relationship with gut microbiome richness and ecology. Gut, 65(3), 426-436. (Year: 2016).*

(Continued)

*Primary Examiner* — Louise W Humphrey
(74) *Attorney, Agent, or Firm* — Houston Beshining Law Office PLLC; Liangang Ye

(57) ABSTRACT

Provided are an *Akkermansia muciniphila* strain and use thereof in preventing and treating metabolic diseases. This strain is named *Akkermansia muciniphila* SSYD-3 and the accession number thereof is CGMCC No. 14764. This strain is more ideal than the existing *Akkermansia* strain ATCC BAA835 in respect of fermentation performance, storage stability, acid and bile resistance, and the effect on treating metabolic diseases.

14 Claims, 5 Drawing Sheets

Specification includes a Sequence Listing.

(56) References Cited

OTHER PUBLICATIONS

Guo, X., Zhang, J., Wu, F., Zhang, M., Yi, M., & Peng, Y. (2016). Different subtype strains of Akkermansia muciniphila abundantly colonize in southern China. Journal of applied microbiology, 120(2), 452-459. (Year: 2016).*

Monaco, G., van Dam, S., Casal Novo Ribeiro, J. L., Larbi, A., & de Magalhães, J. P. (2015). A comparison of human and mouse gene co-expression networks reveals conservation and divergence at the tissue, pathway and disease levels. BMC evolutionary biology, 15(1), 1-14. (Year: 2015).*

Research (2018). Early Clinical Trials With Live Biotherapeutic Products: Chemistry, Manufacturing, and Control Information; Guidance for Industry. U.S. Food and Drug Administration. https://www.fda.gov/regulatory-information/search-fda-guidance-documents/early-clinical-trials-live-b (Year: 2018).*

NCBI "Glucose Metabolism Disorders." www.ncbi.nlm.nih.gov, www.ncbi.nlm.nih.gov/mesh?Db=mesh&Cmd=DetailsSearch&Term=%22Glucose+Metabolism+Disorders%22%5BMeSH+Terms%5D#:~:text=Pathological%20conditions%20in%20which%20the. Accessed Jan. 22, 2024. (Year: 2024).*

Ben Harouch S, Klar A, Falik Zaccai TC. INSR-Related Severe Syndromic Insulin Resistance. Jan. 25, 2018. In: Adam MP, Feldman J, Mirzaa GM, et al., editors. GeneReviews® [Internet]. Seattle (WA): University of Washington, Seattle; 1993-2024. Available from: https://www.ncbi.nlm.nih.gov/books/NBK476444/ (Year: 2018).*

Qi, X., & Tester, R. F. (2019). Fructose, galactose and glucose—In health and disease. Clinical nutrition ESPEN, 33, 18-28. (Year: 2019).*

Liu Z, Hayashi H, Matsumura K, Uemura N, Shiraishi Y, Sato H, Baba H. Biological and Clinical Impacts of Glucose Metabolism in Pancreatic Ductal Adenocarcinoma. Cancers (Basel). Jan. 13, 2023;15(2):498. doi: 10.3390/cancers15020498. PMID: 36672448; PMCID: PMC9856866. (Year: 2023).*

Utzschneider, K. M., Kratz, M., Damman, C. J., & Hullarg, M. (2016). Mechanisms linking the gut microbiome and glucose metabolism. The Journal of Clinical Endocrinology & Metabolism, 101(4), 1445-1454. (Year: 2016).*

Hasani A, Ebrahimzadeh S, Hemmati F, Khabbaz A, Hasani A, Gholizadeh P. The role of Akkermansia muciniphila in obesity, diabetes and atherosclerosis. J Med Microbiol. Oct. 2021;70(10). doi: 10.1099/jmm.0.001435. PMID: 34623232. (Year: 2021).*

Fang, A., Gerson, D. F., & Demain, A. L. Production of Clostridium difficile toxin in a medium totally free of both animal and dairy proteins or digests. Proceedings of the National Academy of Sciences, 106(32), 13225-13229. (Year: 2009).*

Soy Peptone : Shroom Supply. (n.d.). Www.shroomsupply.com. Retrieved Mar. 12, 2024, from https://www.shroomsupply.com/agar-culture-media/bottled-media-mixes-additives/soy-peptone (Year: 2024).*

Sigma Aldrich. Beef extract powder, retrieved on Mar. 19, 2024 https://www.sigmaaldrich.com/us/en/substance/ beefextractpowder 1234568990090?utm_source=google&utm_medium=cpc&utm_campaign=9416925828&utm_content=95899039392&gclid=CjwKCAjw7-SvBhB6EiwAwYdCASnlx_tmY1kNLoDFoDcl_f08stgYViiBiCFEs9Ar4JesQ_R3za (Year: 2024).*

Yeast Extract Powder—Yeast Extract Gluten Free—Benefits of Yeast Extract. (n.d.-a). Aseschem. Retrieved Mar. 13, 2024, from https://ases.in/blogs/news/yeast-extract-powder (Year: 2024).*

Rogers, K. (n.d.). glucose—Britannica Online Encyclopedia. Www.britannica.com. Retrieved Mar. 13, 2024, from https://www.britannica.com/print/article/235853 (Year: 2024).*

"Chemical Safety Facts" Sodium Chloride. (Oct. 14, 2022). Chemical Safety Facts. https://www.chemicalsafetyfacts.org/chemicals/sodium-chloride/#:~:text=Sodium%20chloride%20(NaCl)%2C%20commonly (Year: 2022).*

"Camachem" Top 10 Facts You Need To Know About Magnesium Sulphate. (n.d.). Camachem.com. https://camachem.com/es/blog/post/Magnesium-Sulphate-facts#:~:text=Magnesium%20Sulphate%20is%20a%20naturally%20occurring%20mineral%20and%20can%20be (Year: 2024).*

"Noah Chemicals" Sodium Phosphates | Noah Chemicals. (Oct. 28, 2021). Noahchemicals.com. https://noahchemicals.com/sodium-phosphates/#:~:text=Sodium%20phosphate%20is%20naturally%20occurring (Year: 2021).*

"GLA" Monopotassium Phosphate Aquarium Fertilizer, Green Leaf Aquariums(GLA). Retrieved Mar. 13, 2024, from https://greenleafaquariums.com/products/mono-potassium-phosphate-kh2po4-1lb-bag.html#:~:text=Monopotassium%20Phosphate%20KH2PO4%20%2D%20Fertilizer%20for%20Aquarium&text=Available%20to%20plan (Year: 2024).*

Gregersen, E.. (2018). Pepsin | biochemistry. In Encyclopædia Britannica. https://www.britannica.com/science/pepsin (Year: 2018).*

Oct. 17, 2022 Australian First Office Action issued in Australian Patent Application No. 2019346903.

Sep. 14, 2022 Canadian First Office Action issued in Canadian Patent Application No. 3,114,471.

Dec. 25, 2019 International Search Report issued in International Patent Application No. PCT/CN2019/107757.

Dec. 25, 2019 Written Opinion of the International Searching Authority issued in International Patent Application No. PCT/CN2019/107757.

Zhao et al.,"Characteristics of intestinal bacterium Akkermansia muciniphila and the association with host health" Microbiology China, Jun. 20, 2017, 44(6).

Dao, MC et al.,"Akkermansia muciniphila and improved metabolic health during a dietary intervention in obesity: relationship with gut microbiome richness and ecology GUT"—Jun. 22, 2015, 65(3).

Apr. 5, 2022 Extended European Search Report issued in European Patent Application No. 19864901.4.

"*Akkermansia muciniphila* gen. nov., sp. nov., a human intestinal mucin-degrading bacterium". Derrien M. et al., Int J Syst Evol Microbiol. Sep. 2004;54(Pt 5):1469-1476.

"Test report of WST01 (namely Akkermansia muciniphila SSYD-3)", China Center of Industrial Culture Collection, May 28, 2021.

* cited by examiner

STRAIN FOR PREVENTING AND TREATING METABOLIC DISEASES AND USE THEREOF

CROSS-REFERENCE TO RELATED APPLICATIONS

The Sequence Listing is submitted concurrently with the specification as an ASCII formatted text file via EFS-Web, with a file name of "P20417244US-2-SEQ", a creation date of Mar. 10, 2021, and a size of 2,323 bytes. The Sequence Listing filed via EFS-Web is part of the specification and is incorporated in its entirety by reference herein.

The present application is a National Stage of International Application No. PCT/CN2019/107757, filed on Sep. 25, 2019, which claims priority of the Chinese Patent Application No. CN201811132882.1 filed on Sep. 27, 2018, the contents of which are incorporated herein by reference in their entireties.

BACKGROUND OF THE INVENTION

Field of the Invention

The present invention relates to the field of microorganisms in the field of biotechnology, and specifically relates to a strain for preventing and treating metabolic diseases and use thereof.

Description of Related Art

Obesity is a worldwide health problem. According to the research of the Global Burden of Disease, the global epidemiology of obesity is gradually deteriorating, which has a negative impact on physical hygiene and health economics. Internationally, the body mass index (BMI) is usually used as the standard to judge the degree of obesity. The healthy range for BMI is between 18.5 and 24.9, overweight is defined as a body mass index of 25 or higher, and obese is defined as a body mass index of 30 or higher. Data of a study of 195 countries worldwide showed that the prevalence of obesity has doubled since 1980. At present, 5% of children and 12% of adults are obese. The prevalence of obesity is similar to that of type 2 diabetes, and with this trend, ⅕ of the population worldwide will be obese. From 1975 to 2014, the global average BMI increased from 21.7 to 24.2 kg/m$^2$ for men, and from 22.1 to 24.4 kg/m$^2$ for women. As of 2014, the prevalence of obesity among Chinese adults was 12.9%, the prevalence of overweight was 41.2%, and the prevalence of central obesity was 20.9%, which was increasing year by year. Obesity destroys the metabolic homeostasis of body, which in turn causes metabolic diseases. Obesity is a critical risk factor for the development of type 2 diabetes. Current treatments are mainly to reduce calorie intake and prevent calorie absorption. Gastric volume reduction surgery can reduce energy intake, basic metabolism and exercise can increase calorie consumption and loss, and the increase in brown and beige adipose tissue can increase heat production. In addition, intestinal cells and flora are involved in feeding behavior and can be used as potential targets for treating obesity.

Obesity and type 2 diabetes are affected by environmental and genetic factors. The genes of the human flora also play an important role in both diseases; the flora may affect obesity by influencing, e.g., the absorption of calories, and obesity may in turn affect the composition of intestinal flora. There are more than 1,000 different types of bacteria in the human intestine, with a total of about 1014. Dysbiosis of the intestinal flora is associated with many diseases, including obesity, with a decrease in the anti-inflammatory *Akkermansia muciniphila* (hereinafter referred to as '*Akkermansia*') in obese patient, and an increase in Proteobacteria, *Bacteroides, Campylobacter* and *Shigella* spp. The ratio of Firmicutes to Bacteroidetes not only affects the metabolism of carbohydrates, but also alters the yield of short-chain fatty acids. Increased blood acetic acid levels can lead to increased insulin resistance and ghrelin production, of which the flora may be the most important variable factor. Intestinal flora can change a variety of metabolic pathways centered on energy metabolism balance, thereby affecting the occurrence and development of obesity. Probiotics and prebiotics can play a role in combating obesity by reducing intestinal bacterial lipopolysaccharide, changing the composition of the flora, and reducing fat storage.

Chinese invention patent application with application number CN201380070847.0 and publication number CN104918626A discloses "USE OF *AKKERMANSIA* FOR TREATING METABOLIC DISORDERS", and the *Akkermansia muciniphila* strain ATCC BAA835 screened by this patent application can be used to promote weight loss for subjects in need. However, the inventors had shown through their research that although *Akkermansia muciniphila* strain ATCC BAA835 was generally accepted as the most classic and effective *Akkermansia* strain, the strain was not ideal in respect of fermentation performance, storage stability, acid and bile resistance, and the effect on treating metabolic diseases.

BRIEF SUMMARY OF THE INVENTION

The technical problem to be solved by the present invention is to overcome the defects of the existing *Akkermansia muciniphila* strain ATCC BAA835 in the prior art, which is not ideal in respect of fermentation performance, storage stability, acid and bile resistance, and the effect on treating metabolic diseases. The present invention provides a strain for preventing and treating metabolic diseases and use thereof.

The present invention provides a strain for preventing and treating metabolic diseases. The strain is *Akkermansia muciniphila* strain, which is named *Akkermansia muciniphila* SSYD-3 with an accession number of CGMCC No. 14764 for the deposit.

The present invention provides a use of the *Akkermansia muciniphila* strain in preparing preparations for preventing and treating metabolic diseases.

In the present invention, metabolic diseases have conventional meanings in the art, comprising diabetes, obesity, insulin resistance, alcoholic and non-alcoholic fatty liver, hypertension, hyperlipidemia, hypercholesterolemia, heart disease and other diseases. The preventive and therapeutic effects refer to the prevention of the occurrence and development of metabolic diseases, and the treatment and auxiliary treatment of metabolic diseases, respectively.

In particular, the use of the *Akkermansia muciniphila* strain for treating and preventing metabolic diseases in the present invention comprises one or more of the following uses: for treating and preventing obesity, type 2 diabetes and metabolic syndrome, and other diseases that combine weight gain and glucose metabolism disorders; more preferably, the use comprises: delaying weight gain, reducing visceral adipose tissue, reducing blood-glucose after 15-30 minutes of glucose injection, and reducing fasting blood-glucose and blood-glucose within 60 minutes after insulin injection.

In the present invention, the form of the preparation is a conventional form in the art, comprising medicines, health foods, functional foods, foods, beverages, feed products and dietary supplements containing the *Akkermansia muciniphila*.

In the present invention, the *Akkermansia muciniphila* refers to a living organism or a pasteurized inactivated organism.

In the present invention, the preparation is prepared by using an effective dose of the *Akkermansia muciniphila* as the active ingredient, and adding pharmaceutical excipients such as conventional excipients, flavoring agents, disintegrants, binders, adjuvants, thickers, solubilizers, preservatives, lubricants according to certain preparation techniques. The dosage form is preferably a lyophilized bacterial agent, and the count of viable bacteria is preferably $10^{10}$ CFU/g.

Wherein, the effective dose means that *Akkermansia muciniphila*, as the main active ingredient in a solid viable bacterial preparation, has a viable count of $10^6$-$10^{14}$ CFU/g. Wherein, the effective dose means that *Akkermansia muciniphila*, as the main active ingredient in a liquid viable bacterial preparation, has a viable count of $10^6$-$10^{14}$ CFU/g.

On the basis of the common sense in the art, the abovementioned preferred conditions can be combined arbitrarily to obtain preferred examples of the present invention.

The reagents and raw materials used in the present invention are all commercially available.

The positive and progressive effects of the present invention are as follows: studies in the present invention shows that *Akkermansia muciniphila* SSYD-3 is significantly better than the standard strain of *Akkermansia muciniphila* (ATCC BAA835) in respects of fermentation performance, storage stability, acid and bile resistance, and is significantly better than the standard strain (ATCC BAA835) in respects of delaying weight gain, reducing visceral adipose tissue, reducing blood-glucose after 15-30 minutes of glucose injection, and reducing fasting blood-glucose and blood-glucose within 60 minutes after insulin injection.

DETAILED DESCRIPTION OF THE INVENTION

Figure 1:
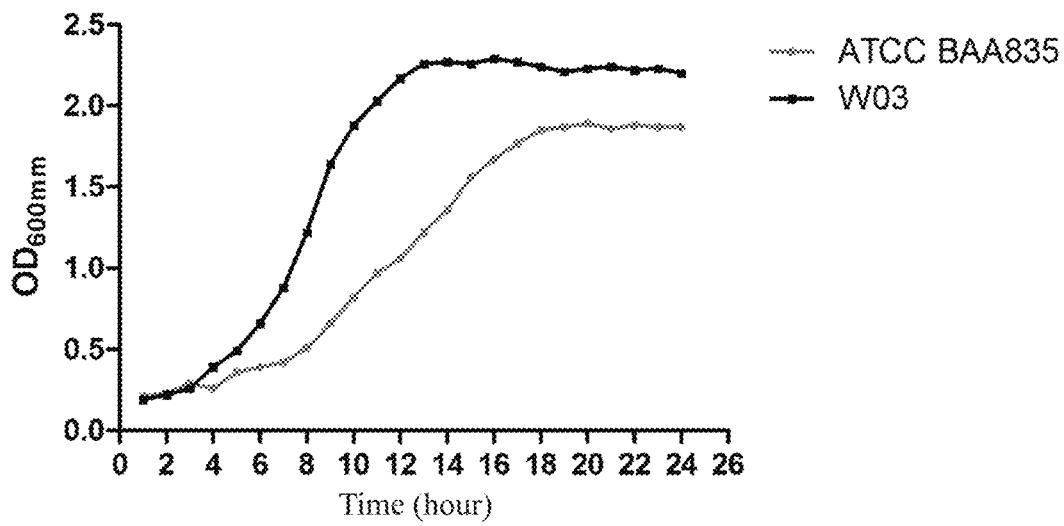
FIG. 1 shows the growth curve of *Akkermansia muciniphila* in Example 3.

The following examples further illustrate the present disclosure, but the present disclosure is not limited thereto.

In the following examples, unless specified otherwise, the experimental methods are selected according to conventional methods and conditions, or according to the product specification.

The experimental data of each group were expressed as mean±standard deviation, and then collated and imported into SPSS18.0 statistical software for data analysis. The difference between the means of each group was tested by analysis of variance. In animal experiments, the data distribution was checked using Shapiro-Wilk, and the homogeneity of variance was further tested using Levene's test. The importance of each two specified groups was assessed using corresponding t-test. P<0.05 means the difference is a statistically significant difference.

Example 1 Screening of Bacteria

1. Culture Medium

Isolation medium: 0.4 g $KH_2PO_4$; 0.53 g $Na_2HPO_4$; 0.3 g $NH_4Cl$; 0.3 g NaCl; 0.1 g $MgCl_2 \cdot 6H_2O$; 0.11 g $CaCl_2$); 0.5 mg resazurin; 4 g $NaHCO_3$; 0.25 g $Na_2S \cdot 7\text{-}9H_2O$; 0.25% mucin.

Fermentation medium 1: brain heart infusion broth (BHI)

Fermentation medium 2: 5 g tryptone, 5 g soybean peptone, 5 g beef powder, 5 g yeast powder, 4 g glucose, 3 g NaCl, 1.5 g $MgSO_4$, $Na_2HPO_4$, $KH_2PO_4$, 1 L water, pH=7.2.

The isolation medium and the fermentation medium were autoclaved at 121° C. for 15 minutes for later use.

2. Isolation and Identification of Strains

① The prepared mucin isolation medium was placed in a serum bottle (liquid volume 10/30 mL).

② 0.5 g stool of healthy adult was placed in sterile PBS (phosphate saline buffer) and dispersed evenly. The stool was 10-fold gradiently diluted in PBS solution, and 1 mL of the dilution was inoculated into the serum bottle containing mucin.

③ The serum bottle containing mucin was placed at 37° C. and incubated for 48 h in an anaerobic environment.

④ The mucin fermentation broth with the highest dilution gradient that was visible to the naked eye was taken and diluted to $10^{-6}$-$10^{-9}$ with PBS buffer.

⑤ The diluent was spread on the brain heart infusion agar medium and incubated for 24-48 hours, and colonies of 1 mm in size was picked, purified and cultured, then the strain identification was performed using bacterial 16S rDNA.

Results: The morphological, physiological and biochemical characteristics of the colonies were combined with the amplification of bacterial 16S rDNA to identify the bacterial species. W03 bacterial 16S rDNA sequence of is shown in SEQ ID No. 1 in the Sequence Listing. Then the sequence obtained by sequencing was compared with the 16S rDNA gene sequence registered in GenBank for homology. Finally, the isolated bacterium was identified to be *Akkermansia muciniphila* and named *Akkermansia muciniphila* SSYD-3, with a maximum sequence similarity of 99% to the existing sequences.

Example 2: *Akkermansia* Fermentation

① *Akkermansia muciniphila* was inoculated on brain heart infusion agar using three sector streak, and incubated anaerobically at 37° C. for 48 hours.

② Single colonies of *Akkermansia muciniphila* were picked from the agar plate and inoculated in 15 mL of brain heart infusion broth, and incubated anaerobically at 37° C. for 24 h.

③ 10 mL fermentation broth was transferred from 15 mL anaerobic tube to 200 mL brain heart infusion broth, and incubated anaerobically at 37° C. for 24 h.

④ 200 mL fermentation broth of *Akkermansia muciniphila* was inoculated into brain heart infusion broth, 4 L of mixed fermentation broth was loaded into a 5 L fermentor. The anaerobic gas was a binary gas mixed by nitrogen and carbon dioxide ($N_2:CO_2=9:1$). The mixed fermentation broth was incubated anaerobically at 37° C. for 24 h with stirring speed of 100 r/min.

Example 3: Fermentation of *Akkermansia muciniphila*

① Single colonies of W03 and standard strain ATCC BAA835 (purchased from the American Type Culture Collection) were respectively inoculated into 15 mL fermentation medium 2, and incubated anaerobically at 37° C. for 24 h.

② 10 mL fermentation broth was transferred from 15 mL anaerobic tube to 200 mL fermentation medium 2, and incubated anaerobically at 37° C. for 24 h.

③ 200 mL *Akkermansia* fermentation broth was inoculated into fermentation medium 2, 4 L of mixed fermentation broth was loaded into a 5 L fermentation tank. The anaerobic gas was a binary gas mixed by nitrogen and carbon dioxide ($N_2:CO_2=9:1$). The mixed fermentation broth was incubated anaerobically at 37° C. for 24 h while controlling pH of 6.5 in the process, until there was no change in OD.

Results: As shown in FIG. 1, the maximum OD of W03 strain was 2.26 ($2.13 \times 10^9$ CFU/mL) after 13 hours of fermentation while the growth of bacteria reached stationary phase, and the maximum OD of ATCC BAA835 was 1.87 ($9.67 \times 10^8$ CFU/mL) after 18 hours of fermentation while the growth of bacteria reached stationary phase. The fermentation time of W03 strain is shorter, which is more conducive to industrial production. The OD during fermentation of W03 strain was significantly higher than that of ATCC BAA835 with a higher fermentation unit.

Example 4: Lyophilized Inoculum of *Akkermansia muciniphila* CGMCC No. 14764

① Lyophilized protectant: trehalose, sucrose and milk powder.

② The fermentation broth obtained in Example 3 was centrifuged at 8000R for 20 minutes to collect the bacteria.

③ The bacteria obtained by centrifugation of *Akkermansia muciniphila* was mixed with lyophilized protectant and water to make sure the mass percentages of trehalose, sucrose and milk powder in the solution were 5%, 5% and 10% respectively before lyophilization. Then the solution was lyophilized to obtain a lyophilized bacterial powder, and the number of viable bacteria of the *Akkermansia muciniphila* strain with the accession number of CGMCC No. 14764 for the deposit in the bacterial powder was $10^{10}$ CFU/g.

Comparative Example 1: Lyophilized Inoculum of *Akkermansia muciniphila* Strain ATCC BAA835

The preparation method and parameter conditions of the lyophilized bacterial inoculum in Comparative Example 1 are the same as those in Example 4, except that the strain is *Akkermansia muciniphila* strain ATCC BAA835.

Example 5: Storage Stability of *Akkermansia muciniphila* Powder

W03 bacterial powder obtained in Example 4 and ATCC BAA835 bacterial powder obtained in Comparative Example 1 were stored at 4° C. for 24 months and at 25° C. for 6 months to compare their storage stability.

Figure 2:
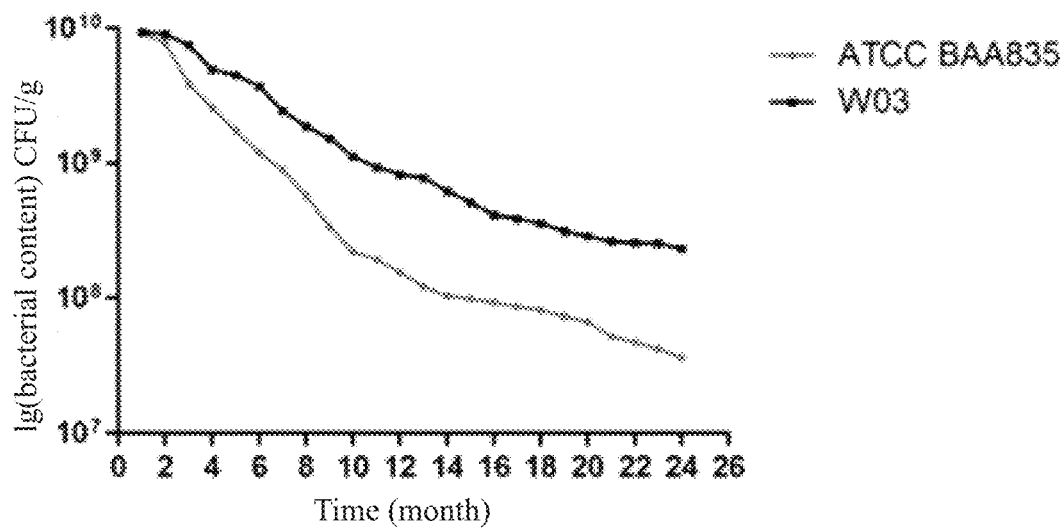
FIG. 2 shows the variation curve of the bacterial content of *Akkermansia muciniphila* in Example 5 under the storage condition of 4° C.
Figure 3:
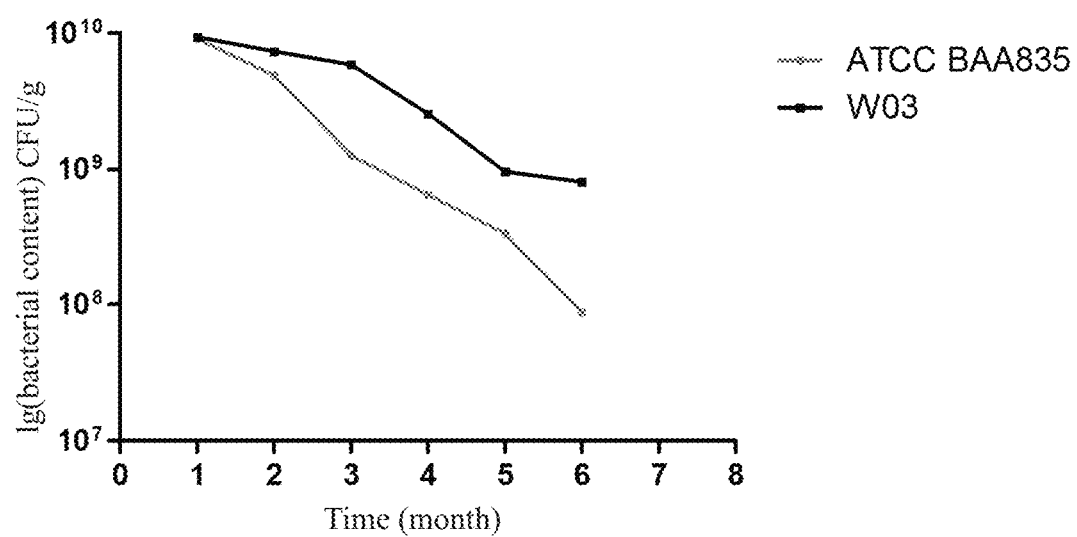
FIG. 3 shows the variation curve of the bacterial content of *Akkermansia muciniphila* in Example 5 under the storage condition of 25° C.

Results: It can be seen from FIG. 2 that after 2 years of storage at 4° C., the number of viable bacteria of W03 bacterial powder is $4.85 \times 10^8$ CFU/g, which was one order of magnitude higher than that of ATCC BAA835 bacterial powder ($6.69 \times 10^7$ CFU/g). This means that W03 strain is more stable and has a longer shelf life. It can be seen from FIG. 3 that after 6 months of storage at 25° C., the number of viable bacteria of W03 bacterial powder was $8.23 \times 10^8$ CFU/g, which was one order of magnitude higher than that of ATCC BAA835 bacterial powder ($7.79 \times 10^7$ CFU/g). This means that W03 strain is more stable in storage.

Example 6: Viability of *Akkermansia muciniphila* in Simulated Gastric Juice 2.0 sodium chloride and 3.2 g pepsin were dissolved in 7.0 ml hydrochloric acid and water and the solution was replenished to 1000 mL. The artificial gastric juice with pH 1.2 was filtered through 0.22 μm filter to get sterilized. 20 ml sterilized artificial gastric juice was filled into 30 mL sterile vials with a total of 3 vials, then sealing the vials with aluminum caps, and the headspace gas was replaced with nitrogen for protection. The lyophilized bacterial powder of W03 and ATCC BAA835 was each added to 1 mL sterile PBS, and 1 mL of the bacterial suspensions was each inoculated into the above vials. The vials were placed at 37° C., and the solutions were sampled at different times to calculate the survival rate.

Results: The viability of two strains in a simulated gastric juice environment was investigated in this experiment. It can be seen from Table 1 that the survival rates of the two strains showed a significant downward trend with time. The survival rate of W03 was higher than that of ATCC BAA835 at different times, and W03 had stronger acid tolerance.

TABLE 1

Viability of *Akkermansia muciniphila* in simulated gastric juice

| Strain | 0 h | 1 h | 2 h | 3 h | 4 h | 2 h viability |
|---|---|---|---|---|---|---|
| W03 ($10^9$ CFU/mL) | 6.35 | 5.68 | 4.32 | 1.32 | 1.04 | 68.03% |
| ATCC BAA835 ($10^9$ CFU/mL) | 6.52 | 4.52 | 3.18 | 1.19 | 0.67 | 48.77% |

Example 7: Viability of *Akkermansia muciniphila* in Simulated Intestinal Juice 6.8 g of potassium dihydrogen phosphate and 3 g of bile salt No. 3 were added into 500 mL of water, followed by adjusting the pH to 6.8 with 0.4% sodium hydroxide solution; then 10 g of pancreatin was dissolved in appropriate amount of water. After mixing the two liquids, the mixed solution was replenished to 1000 mL with water, then filtered with 0.22 μm filter membrane for sterilization. 20 ml sterilized artificial gastric juice was filled into 30 mL sterile vials with a total of 3 vials, then sealing the vials with aluminum caps, and the headspace gas replaced with nitrogen for protection. The lyophilized bacterial powder of W03 and ATCC BAA835 was each added to 1 mL sterile PBS, and 1 mL of the bacterial suspensions was each inoculated into the vials described above. The vials were placed at 37° C., and the solutions were sampled at different times to calculate the survival rate.

Results: It can be seen from Table 2 that under the same conditions, W03 strain has better bile tolerance than the control strain ATCC BAA 835, and W03 strain is more conducive to resist high bile salt environment to colonize the intestine.

TABLE 2

Viability of *Akkermansia muciniphila* in simulated intestinal juice

| Strain | 0 h | 1 h | 2 h | 3 h | 4 h | 2 h viability |
|---|---|---|---|---|---|---|
| W03 ($10^9$ CFU/mL) | 6.16 | 1.70 | 1.32 | 1.04 | 0.88 | 21.43% |
| ATCC BAA835 ($10^9$ CFU/mL) | 6.29 | 1.23 | 0.87 | 0.81 | 0.75 | 13.83% |

Example 8: Application of *Akkermansia muciniphila* for Treating Metabolic Diseases Eight-week-old male C57 BL/6 mice (no specific pathogens, Shanghai Lab Animal Research Center) were fed food ad libitum in groups of 3 mice per cage (filter cage) during a strict 12-hour photoperiod. After adapting to the new environment, they were fed a standard diet or a high-fat diet with 60 kcal % fat (Research Diet, D12492i). The animals were randomly allocated into 2 groups and administrated with 200 microliters of sterile PBS and *Akkermansia muciniphila* bacterial solution ($10^8$ CFU/100 microliters), respectively, once a day for 8 weeks.

Body weight was measured before intragastric administration and at the end of the experiment. The food intake of 7 consecutive days was recorded by cage (3 mice per cage) to calculate the average food intake per mouse per day. Stool samples were collected before intragastric administration and at the end of the experiment, and immediately stored in a refrigerator at −80° C. for further analysis. Body fat content was assessed with a body composition analyzer (EchoMRI™). Whole blood was collected from the tail vein of mice, and the blood glucose level and insulin level were measured with a glucometer (© LifeScan). To ensure that the starting points were the same, this study did not use random allocation, but grouped mice that had adapted to the environment according to their body weight. All operations were approved by the Animal Ethics Committee of Shanghai Jiaotong University School of Medicine.

Figure 4:
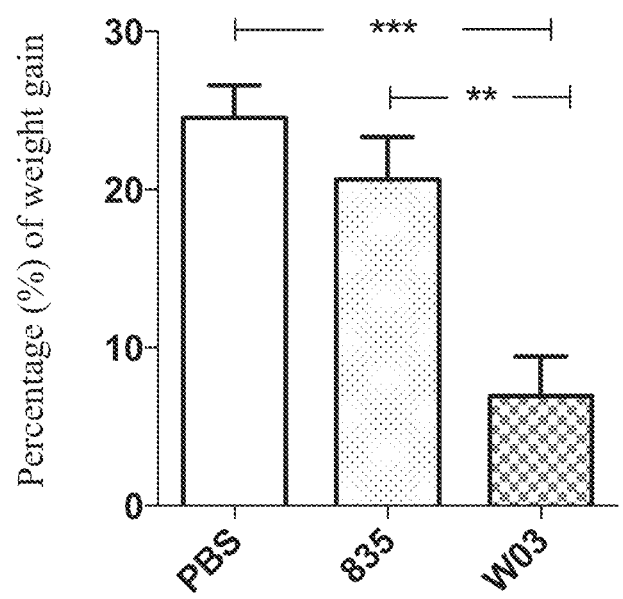
FIG. 4 shows the weight gain results of the mice that was administrated with W03 and ATCC BAA835 in Example 8.

The experimental results are as follows:

1. W03 delays the weight gain of obese mice induced by high-fat diet with better effect than PBS and positive control ATCC BAA835. The weight gain percentage of mice administrated with W03 is lower than that of ATCC BAA835 mice with a significant difference,  $p<0.01$ (FIG. 4**: n=9-10 per group, indicating by mean±standard error, * means the difference is statistically significant, * $p<0.05$,  $p<0.01$, * $p<0.001$).

Figure 5:
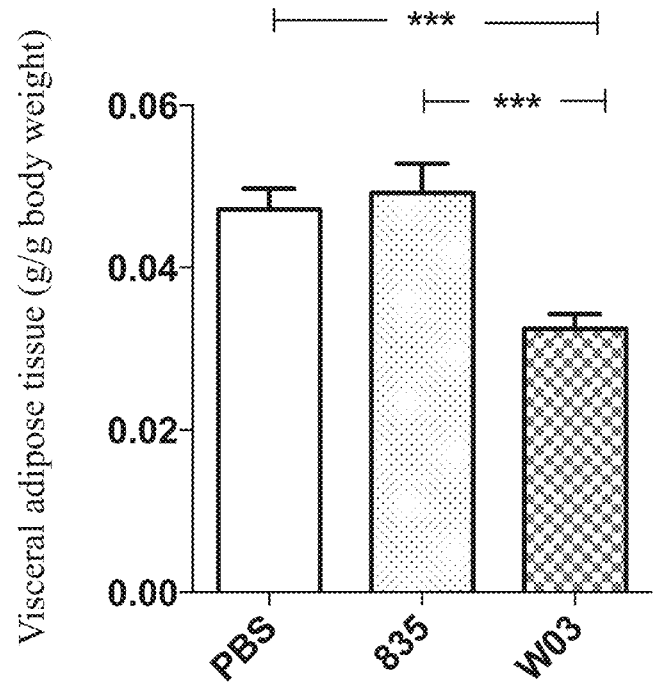
FIG. 5 shows the visceral adipose tissue of the mice that was administrated with W03 and ATCC BAA835 in Example 8.

2. The application of W03 reduces the visceral adipose tissue of obese mice fed with high-fat diet, the effect is superior to the positive control ATCC BAA835 with a significant difference, * $p<0.001$; there is no significant difference between ATCC BAA835 and PBS control group, i.e., $P>0.05$, indicating that ATCC BAA835 strain does not improve the visceral adipose tissue of high-fat obese mice (FIG. 5**: n=9-10 per group, indicating by mean±standard error, * means the difference is statistically significant,* $p<0.05$,  $p<0.01$, * $p<0.001$). Visceral adipose deposition is the main feature of central obesity, while visceral adipose is considered to be significantly associated with obesity-related metabolic complications such as insulin resistance and cardiovascular risk events. Therefore, reducing the visceral adipose tissue has a good preventive effect on the occurrence of metabolic-related complications and cardiovascular risk events in obese patients.

Figure 6:
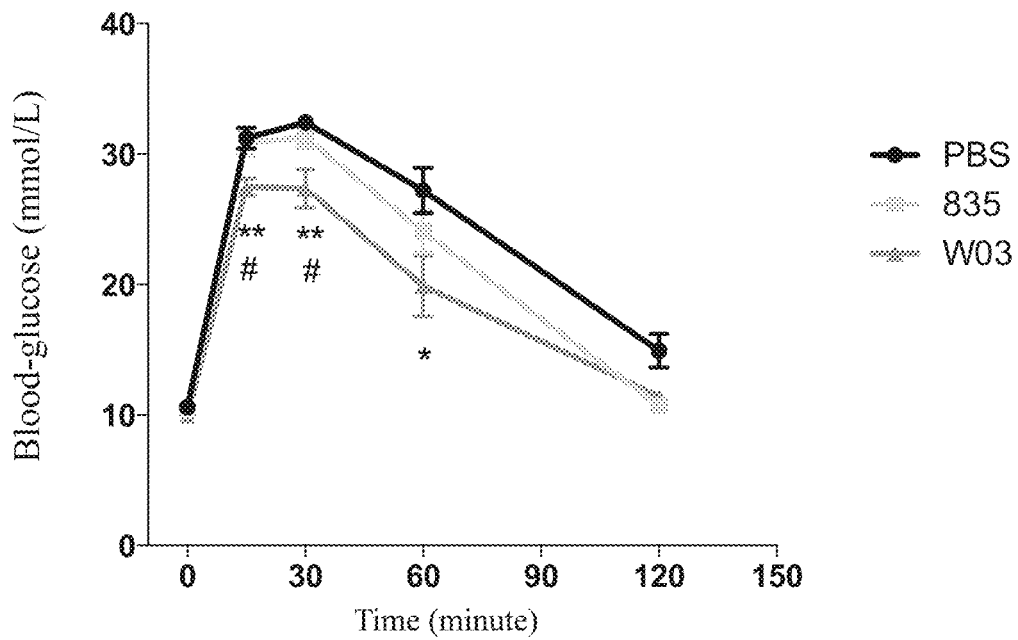
FIG. 6 shows the glucose tolerance of the mice that was administrated with W03 and ATCC BAA835 after intraperitoneal injection of gluc in Example 8.

3. The application of W03 improves the glucose tolerance of obese mice fed with high-fat diet, whose blood-glucose is significantly lower than the positive control ATCC BAA835 group after 15 min and 30 min of glucose injection, with significant differences at 15 min and 30 min (FIG. 6: n=9-10 per group, indicating by mean±standard error, * means the difference is statistically significant compared with PBS, #means the difference is statistically significant compared with ATCC BAA835* #$p<0.05$,  ##$p<0.01$, * ###$p<0.001$). High-fat diet can cause impaired glucose regulation, while W03 treatment can alleviate the degree of impairment, which manifested as that the tolerance of mice with intraperitoneal glucose injection is improved compared with the PBS group. The improvement of glucose tolerance after the application of W03 is more significant than that of ATCC BAA835, and the effect is better than the positive control ATCC BAA835. It is suggested that W03 can improve the impaired glucose regulation in pre-diabetes, which has a certain contribution to preventing the occurrence and development of diabetes.

Figure 7:
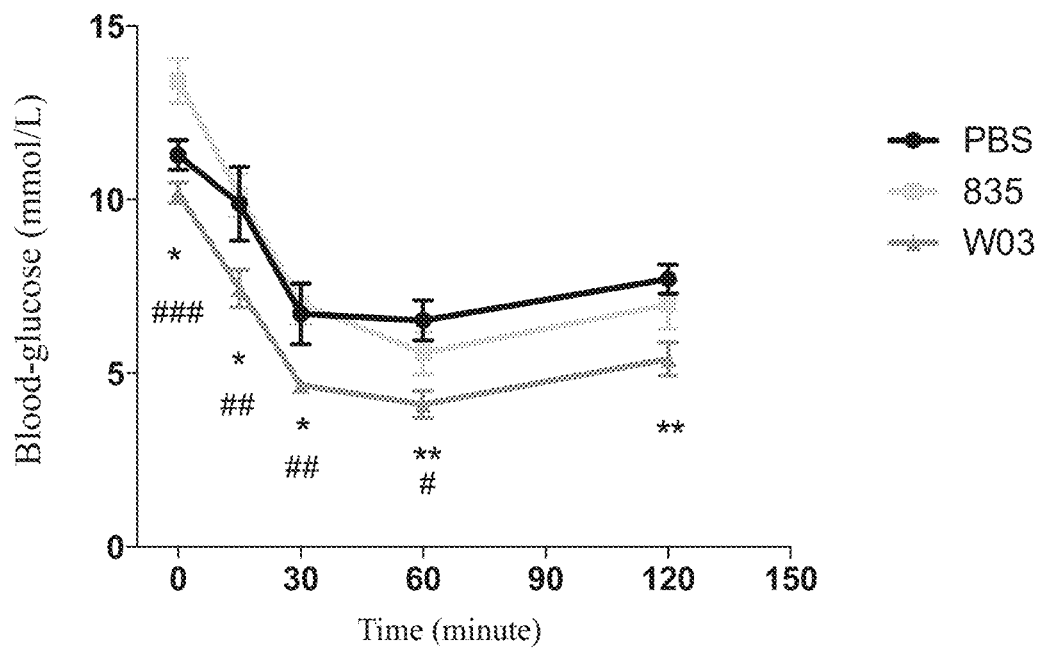
FIG. 7 shows the blood-glucose of the mice that was administrated with W03 and ATCC BAA835 after intraperitoneal injection of insulin in Example 8.

4. The application of W03 improves the insulin tolerance of obese mice fed with high-fat diet, which manifested as the fasting blood-glucose and blood-glucose at 15 min, 30 min, 60 min and 120 min after insulin injection are all lower than the control group PBS, wherein the fasting blood-glucose and blood-glucose at 15 min, 30 min, 60 min and 120 min after insulin injection are even better than the positive control ATCC BAA835 (FIG. 7: n=9-10 per group, indicating by mean±standard error, * means the difference is statistically significant compared with PBS, #means the difference is statistically significant compared with ATCC BAA835*#$p<0.05$,  ##$p<0.01$, * ###$p<0.001$). High-fat diet leads to decreased insulin sensitivity and deterioration of insulin tolerance, while the application of W03 can alleviate the deterioration of insulin tolerance induced by high-fat diet, with better effect than the positive control ATCC BAA835. It is suggested that the application of W03 can benefit patients with reduced insulin sensitivity, thereby preventing the occurrence and development of diabetes.

Figure 8:
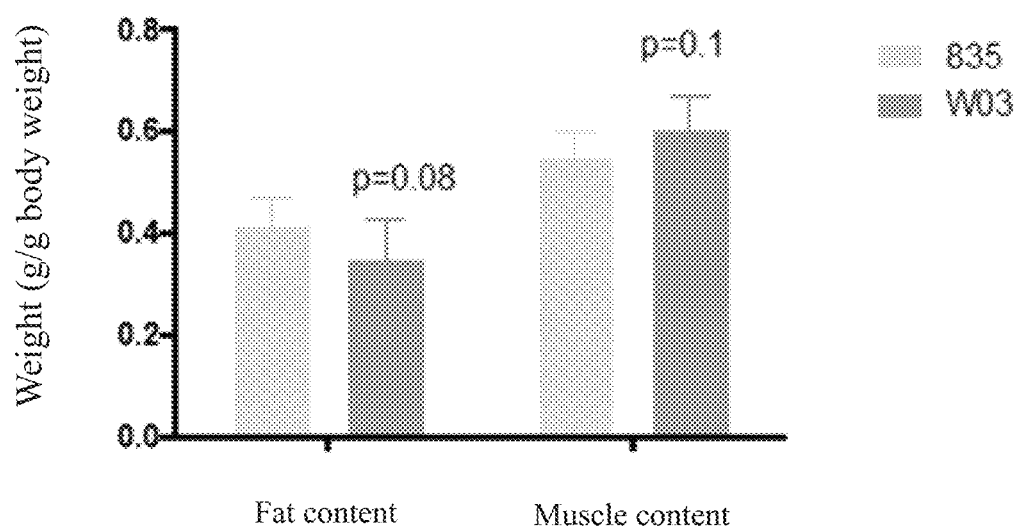
FIG. 8 shows the change in body fat of the mice that was administrated with W03 and ATCC BAA835.

5. The body fat composition of the model animals in this study is relatively complicated. In addition to the measurable inguinal fat (subcutaneous fat) and paradidymal fat (visceral adipose), there is lots of fat that is hard to collect and measure like omental fat. Therefore, the body composition of the model animal was analyzed with a small animal body fat imager, and the results are shown in FIG. 8. The results show that compared with the original strain ATCC BAA835, the visceral adipose tissue of model animals applied with W03 is reduced, and the increase in non-body fat content (muscles, bones, etc.) is obvious.

The positive clinical significance in pharmacodynamic experiments is as follows:

Nearly 50% of obese patients have 'Triple-H' symptoms, i.e. hyperglycemia, hyperlipidemia, and hypertension. Visceral adipose deposition is the main feature of central obesity. Meanwhile, visceral adipose is considered to be significantly associated with insulin resistance, cardiovascular and cerebrovascular risk events and other obesity-associated metabolic complications. Therefore, reducing the visceral adipose tissue has a good preventive effect on the occurrence of the dangerous events described above. In respect of improving oral glucose tolerance, mice administrating with W03 showed a 3-4 mmol/L reduction in intravenous blood-glucose at 30 min and 60 min postprandial, thus allowing for 1.5-2 U less insulin or one less second-line hypoglycemic drug for non-severe diabetic patients clinically. The use of W03 can also improve the intravenous insulin tolerance of high-fat-induced obese mice. Its practical significance is that a large part of insulin resistance is caused by fat accumulation, therefore improving insulin resistance can also slow down the progression of pre-diabetes to diabetes and reduce insulin dosage in patients that were injected with insulin. Because long-term clinical use of insulin has the risk of weight gain, reducing the amount of insulin used is of great practical significance for obese patients with diabetes. Meanwhile, many drugs need to be metabolized and detoxified by the liver, and the livers of obese patients have low inflammation and a slightly abnormal liver function. Reducing the use of drugs is of great significance to reduce the body burden and cost for treatment of the patients with chronic diseases such as obesity or obesity with diabetes.

Information of Deposit of Microorganism Material

The *Akkermansia muciniphila* SSYD-3 (strain W03 for short) of the present invention has been deposited in China General Microbiological Culture Collection Center (CGMCC) on Sep. 29, 2017. The deposit address: Building 3, Lane 1, NO. 1 West Beichen Road, Chaoyang District, Beijing 100101, the accession number is CGMCC No. 14764, the culture name is *Akkermansia muciniphila* SSYD-3, and the proposed taxonomic name is *Akkermansia muciniphila*. The above deposit was made under the terms of the Budapest Treaty. Upon issuance of a patent, the deposit will be irrevocably and without restriction released to the public.

Although specific embodiments of the present invention have been described above, those skilled in the art should understand that these are merely illustrative, and various changes or modifications can be made to the present invention without departing from the principles and spirits of the present invention. Therefore, the protection scope of the present invention is defined by the appended claims.

What is claimed is:

1. A method for treating a metabolic disease in a subject in need thereof, comprising: administering a preparation comprising a strain and a lyophilized protectant to the subject;
   wherein the strain is an *Akkermansia muciniphila* strain, which is named *Akkermansia muciniphila* SSYD-3 deposited under CGMCC No. 14764;
   the metabolic disease is obesity or type 2 diabetes.

2. The method of claim 1, wherein the preparation comprises an effective dose of the *Akkermansia muciniphila* strain and pharmaceutical excipients.

3. The method of claim 1, wherein the preparation is a lyophilized bacterial inoculum, which has a count of $10^{10}$ CFU/g viable bacteria of the *Akkermansia muciniphila* strain.

4. The method of claim 2, wherein the effective dose is a solid viable preparation of $10^6$-$10^{14}$ CFU/g of the *Akkermansia muciniphila* strain.

5. The method of claim 2, wherein the effective dose is a liquid viable preparation of $10^6$-$10^{14}$ CFU/g of the *Akkermansia muciniphila* strain.

6. The method of claim 1, wherein administration of the preparation serves one or more of the following functions: delaying weight gain, reducing visceral adipose tissue, reducing blood-glucose 15 min-30 min after glucose injection, and reducing fasting blood-glucose and blood-glucose within 60 minutes after insulin injection.

7. A method for treating a metabolic disease in a subject in need thereof, comprising: administering an effective dose of a strain to the subject, wherein the strain is *Akkermansia muciniphila* SSYD-3 deposited under CGMCC No. 14764;
   the metabolic disease is obesity or type 2 diabetes.

8. The method of claim 7, wherein the effective dose is $10^6$-$10^{14}$ CFU/g of *Akkermansia muciniphila* SSYD-3.

9. The method of claim 7, wherein administration of the preparation serves one or more of the following functions: delaying weight gain, reducing visceral adipose tissue, reducing blood-glucose 15 min-30 min after glucose injection, and reducing fasting blood-glucose and blood-glucose within 60 minutes after insulin injection.

10. The method of claim 1, wherein the preparation is a lyophilized bacterial inoculum, which has a count of $10^6$-$10^{14}$ CFU/g viable bacteria of the *Akkermansia muciniphila* strain.

11. The method of claim 10, wherein the lyophilized protectant comprises trehalose, sucrose and milk powder.

12. The method of claim 11, wherein the trehalose, sucrose and milk powder have mass percentages of 5%, 5% and 10% respectively in a solution of the trehalose, sucrose and milk powder before lyophilization.

13. The method of claim 1, wherein the strain serves one or more of the following functions:
   a) maximum OD of the strain is higher than 1.87 ($9.67 \times 10^8$ CFU/mL) after 18 hours of fermentation;
   b) number of viable bacteria of the strain is higher than $7.79 \times 10^7$ CFU/g after 6 months of storage at 25° C.;
   c) viability of the strain in simulated gastric juice for 2 h is higher than 48.77%; and,
   d) viability of the strain in simulated intestinal juice for 2 h is higher than 13.83%.

14. The method of claim 7, wherein the strain serves one or more of the following functions:
   a) maximum OD of the strain is higher than 1.87 ($9.67 \times 10^8$ CFU/mL) after 18 hours of fermentation;
   b) number of viable bacteria of the strain is higher than $7.79 \times 10^7$ CFU/g after 6 months of storage at 25° C.;
   c) viability of the strain in simulated gastric juice for 2 h is higher than 48.77%; and,
   d) viability of the strain in simulated intestinal juice for 2 h is higher than 13.83%.

\* \* \* \* \*

SEQUENCE LISTING

<160> NUMBER OF SEQ ID NOS: 1

<210> SEQ ID NO 1
<211> LENGTH: 1421
<212> TYPE: DNA
<213> ORGANISM: Akkermansia muciniphila

<400> SEQUENCE: 1

```
gaccccgtct aaccttagga ccctgcctcc ttgcggttgg cttcagatac ttcgggtgcg      60
accggcttcc atgatgtgac gggcggtgtg tacaagaccc gggaacgtat tcacgcgcc      120 gtagctgatg cgccattact agcgattccg gcttcgtgta ggcgggttgc agcctacagt     180
ccgaactggg cccagttttt aggatttcct ccgcctcgcg gcttcggccc cctctgtact     240
gggcattgta gtacgtgtgc agccctgggc ataagggcca tactgacctg acgtcgtccc     300
caccttcctc ccagttgatc tgggcagtct cgccagagtc cccaccttca cgtgctggta     360
actggcaaca ggggttgcgc tcgttgctgg acttaaccaa acatctcacg acacgagctg     420
acgacggcca tgcagcacct gtgtaacgcc tccgaagagt cgcatgcttt cacatgttgt     480
tcattacatg tcaagcccag gtaaggttct tcgcgttgca tcgaattaag ccacatactc     540
caccgcttgt gcgggtcccc gtcaatttct ttgagtttta atcttgcgac cgtactcccc     600
aggcggcacg cttaacgcgt tagctccggc acgcaggggg tcgattcccc gcacaccaag     660
cgtgcaccgt ttactgccag gactacaggg gtatctaatc cctttcgctc ccctggcctt     720
cgtgcctcag cgtcagttaa tgtccaggaa cccgccttcg ccacgagtgt tcctctcgat     780
atctacgcat tcactgcta caccgagaat tccggttccc cctccattac tctagtctcg     840
cagtatcatg tgccgtccgc gggttgagcc cgcgcctttc acacgact tacgaaacag     900 cctacgcacg ctttacgccc agtgattccg aacaacgctt gagacctctg tattaccgcg     960
gctgctggca cagagttagc cgtctcttcc tcttgtggta ctatcttttt aatttgctcc    1020
cacatgacag gggtttacaa tccgaagacc ttcattcccc cacgcggcgt cgcaccatca    1080
gggtttcccc cattgtgaat gattctcgac tgctgccacc cgtaggtgtc tggaccgtgt    1140
ctcagttcca gtgtggccgg acatcctctc agaccggcta cccgtcatcg ccttggtgag    1200
ccgttacctc accaactaac taataggccg cgagcccatc cccaagcgca ttgctgcttt    1260
```

```
aatctttcga tactatgcgg tattaatccc agtttcccag ggctatcccg ctctcggggg    1320
caggttactc acgtgttact cacccgtgcg ccactagaga attattagca agctagcaat    1380
tctctcgttc gacttgcatt ctaagcaggc cggccacggc c                        1421
```